United States Patent [19]

Yamamoto et al.

[11] Patent Number: 5,756,123
[45] Date of Patent: May 26, 1998

[54] CAPSULE SHELL

[75] Inventors: Taizo Yamamoto, Osaka; Seinosuke Matsuura, Souraku-gun; Kazukiyo Akai, Kashihara, all of Japan

[73] Assignee: Japan Elanco Co., Ltd., Osaka, Japan

[21] Appl. No.: 797,622

[22] Filed: Feb. 7, 1997

Related U.S. Application Data

[63] Continuation-in-part of Ser. No. 548,265, Oct. 25, 1995, abandoned.

[30] Foreign Application Priority Data

Dec. 1, 1994 [JP] Japan .................... 6-323581
Dec. 16, 1994 [JP] Japan .................... 6-333965

[51] Int. Cl.⁶ ......................................... A61K 9/48
[52] U.S. Cl. .................... 424/451; 424/452; 424/455; 424/494
[58] Field of Search ........................ 424/451, 494, 424/452, 455

[56] References Cited

U.S. PATENT DOCUMENTS

| | | | |
|---|---|---|---|
| 3,617,588 | 11/1971 | Langman | 264/486 |
| 4,001,211 | 1/1977 | Sarkar | 536/84 |
| 4,993,137 | 2/1991 | Muto et al. | 29/451 |
| 5,032,074 | 7/1991 | Muto et al. | 425/272 |
| 5,264,223 | 11/1993 | Yamamoto et al. | 424/451 |
| 5,431,917 | 7/1995 | Yamamoto et al. | 424/451 |

FOREIGN PATENT DOCUMENTS

| | | |
|---|---|---|
| 0592130 | 4/1994 | European Pat. Off. |
| 2029402 | 6/1970 | Germany |
| 47-4310 | 2/1972 | Japan |
| 61-100519 | 5/1986 | Japan |
| 62-266060 | 11/1987 | Japan |
| 3-279325 | 12/1991 | Japan |

*Primary Examiner*—Amy Hulina
*Attorney, Agent, or Firm*—Birch, Stewart, Kolasch & Birch, LLP

[57] ABSTRACT

A capsule shell comprising 79.6–98.7% by weight of a hydroxypropylmethyl cellulose, 0.03–0.5% by weight of carrageenan, and 0.14–3.19% by weight of a potassium ion and/or a calcium is prepared by drying an solution comprising 18–28% by weight of hydroxypropylmethyl cellulose whose 2% aqueous solution has a viscosity of 2.4–5.4 centistokes at 20° C. as a base, 0.01–0.09% by weight of carrageenan as a gelling agent, and 0.05–0.6% by weight of a potassium ion and/or calcium ion as a co-gelling agent. The capsule shell exhibits disintegrating ability equivalent to gelatin shells without degrading that ability even under special conditions containing much calcium ions.

8 Claims, 2 Drawing Sheets

FIRST FLUID

SECOND FLUID

CAPSULE SHELL

CROSS REFERENCE TO RELATED APPLICATION

This application is a continuation-in-part of copending application Ser. No. 08/548,265 filed on Oct. 25, 1995 the entire contents of which are hereby incorporated by reference.

BACKGROUND OF THE INVENTION

1. Field of the Invention

This invention relates to a capsule shell for forming medical hard capsules. More particularly, it relates to such a capsule shell using hydroxypropylmethyl cellulose as a base.

2. Prior Art

Medical hard capsules are conventionally formed from compositions comprising gelatin as a base with a plasticizer such as glycerin and sorbitol, opaque agent, dye, pigment and other additives blended therein. After molding pins are immersed in a gelatin aqueous solution with such components blended and withdrawn therefrom, the gelatin solution adhering to the pins is dried, obtaining capsule shells.

The shell-forming compositions based on gelatin have the problem that the plasticity and other properties of shells largely depend on a water content. With a too low water content, shells are less resistant against shocks as encountered on drug filling. Also, as the water content lowers due to drying during shelf storage, shells can contract to loosen the cap-body engagement of capsules.

For gelatin capsules, it is thus critical to maintain the water content constant. However, since the optimum water content is as high as about 10 to 15% by weight, there is a likelihood that the water in the capsule shell can affect the drug fill to lower its titer, degrade its quality, and change its color, and inversely, the capsule shell can be insolubilized if the drug fill is susceptible to hydrolysis or is a mixture of interacting ingredients. Therefore, there is a demand to have capsules based on a substance other than gelatin so that the material of capsules can be selected in accordance with a particular drug fill.

Medical capsules using a base other than gelatin are known in the art. Typically, capsules based on water-soluble cellulose derivatives were proposed. For example, Japanese Patent Publication (JP-B) No. 4310/1972 discloses a method for preparing capsules based on water-soluble cellulose ether from an aqueous solution of water-soluble cellulose ether. Japanese Patent Application Kokai (JP-A) Nos. 100519/1986 and 266060/1987 discloses to prepare capsules from an aqueous solution of water-soluble cellulose ether and polyvinyl alcohol (PVA) blended therewith.

The former shell-forming method involves the steps of immersing molding pins in an aqueous solution of water-soluble cellulose derivative and heating the pins and hence, the coating adhered thereto for gelation. The coating is not gelled or solidified and can fall down from the pins if heating is insufficient. The coating can be wrinkled during gelation if the heating temperature is too high. In the latter method of preparing capsules from an aqueous solution of water-soluble cellulose derivative and PVA, the water-soluble cellulose derivative adhered to the molding pins is gelled by immersing it in hot water. Some of the gelled coating can be dissolved in the hot water at this point, hindering formation of uniform shells. In addition, due to low jelly strength, the dried shells can be often cracked upon removal from the molding pins. In either of these methods, it is difficult to produce capsule shells having a low water content.

Additionally, these methods require a special apparatus or operation of heating the molding pins or immersing the molding pins with cellulose coating in hot water. Unfortunately, it is impossible to utilize the current manufacturing apparatus for gelatin capsules without a substantial change.

To solve these problems, the applicant previously proposed in U.S. Pat. No. 5,264,223 a medical hard capsule having a low water content which is shaped from a capsule shell composition comprising a water-soluble cellulose derivative as a base, a gelling agent and a co-gelling agent. This capsule has equivalent performance to conventional gelatin capsules and can be produced by utilizing the current manufacturing apparatus for gelatin capsules as such.

However, through the continuing research works of the inventors, it was found that this capsule is inferior to conventional gelatin capsules in solubility or disintegrating ability under certain conditions. More particularly, one preferred formulation of this capsule shell composition uses hydroxypropylmethyl cellulose as a water-soluble cellulose derivative base, carrageenan as a gelling agent and a potassium ion as a co-gelling agent. Shells of this preferred formulation take a long time to disintegrate under special conditions where calcium ions are present. Then, if a capsule of this composition filled with drugs is administered after having a food or beverage containing much calcium ions, for example, milk, then the capsule is retarded from disintegration. Then the drugs are not fully released or absorbed within a proper time, failing to fully exert their pharmaceutical effect. Therefore, it is desired to further improve the properties of the capsule based on a water-soluble cellulose derivative.

SUMMARY OF THE INVENTION

An object of the present invention is to provide a capsule shell based on a water-soluble cellulose derivative which does not degrade its disintegration ability under special conditions where much calcium ions are present, that is, exerts its performance under any condition.

In connection with the capsule shell composition comprising hydroxypropylmethyl cellulose (to be abbreviated as HPMC, hereinafter) as a water-soluble cellulose derivative base, carrageenan as a gelling agent, and a potassium ion as a co-gelling agent wherein the shapability of HPMC is improved by blending carrageenan as a gelling agent and gelling this carrageenan with the co-gelling agent, we found that the disintegration ability of this composition is degraded in the presence of calcium ions because the calcium ions inhibit dissolution of the carrageenan blended in the composition as the gelling agent.

Continuing research works, we have found that degradation of the disintegration ability due to the presence of calcium ions is restrained by using a larger proportion of a EPMC having a relatively low viscosity as a base, increasing the amount of the co-gelling agent blended, and minimizing the proportion of carrageenan gelling agent within a sufficient range to insure good shapability. More particularly, by using a HPMC having a viscosity of 2.4 to 5.4 centistokes as measured in a 2t aqueous solution at 20° C., blending the HPMC with carrageenan as a gelling agent and a co-gelling agent in the water to form an aqueous solution comprising 18 to 28% by weight of the HPMC, 0.01 to 0.09% by weight of carrageenan and 0.05 to 0.6% by weight of a co-gelling agent, and drying the aqueous solution to form a capsule shell comprising 79.6 to 98.7% by weight of the HPMC, 0.03 to 0.5% by weight of carrageenan, and 0.14 to 3.19% by weight of a co-gelling agent, there is obtained a capsule shell which maintains satisfactory disintegration ability even in the presence of calcium ions and exerts performance equivalent to conventional gelatin capsules. A hard capsule for pharmaceutical drugs of the capsule shell can be securely and efficiently produced according to the conventional immersion molding.

Accordingly, the present invention provides a capsule shell comprising 79.6 to 98.7% by weight of a hydroxypropyl-methyl cellulose, 0.03 to 0.5% by weight of carrageenan, and 0.14 to 3.19% by weight of a potassium ion and/or a calcium ion, said capsule shell being prepared by drying an aqueous solution comprising 18 to 28% by weight of hydroxypropyl-methyl cellulose having a viscosity of 2.4 to 5.4 centistokes as measured in a 2% aqueous solution at 20° C. as a base, 0.01 to 0.09% by weight of carrageenan as a gelling agent, and 0.05 to 0.6% by weight of at least one ion selected from the group consisting of potassium and calcium ions as a co-gelling agent.

BEST MODE FOR CARRYING OUT THE INVENTION

Figure 1A:
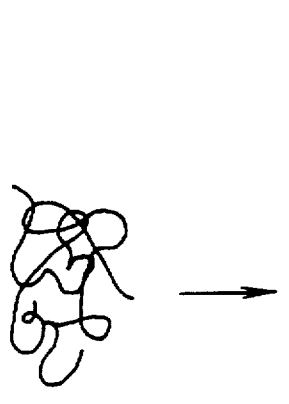
FIGS. 1(A), 1(B) and 1(C) schematically illustrate the gelation mechanism of carrageenan.

In a capsule shell consisting essentially of HPMC as a base, carrageenan as a gelling agent, a co-gelling agent for assisting in gelation of carrageenan and water, the present invention optimizes the viscosity of HPMC and the blending proportion of the respective components such that the capsule shell may maintain satisfactory disintegration ability even under special conditions where much calcium ions are present.

The HPMC used as the base may be a commercially available powder product. According to the invention, the HPNC should be a low viscosity one such that a 2% aqueous solution of HPMC has a viscosity of 2.4 to 5.4 centistokes at 20° C., preferably 3.0 to 4.6 centistokes at 20° C. As defined herein, the viscosity of HPMC is not the viscosity of HPMC itself, but the viscosity of a 2% aqueous solution of HPMC throughout the specification. With a viscosity of less than 2.4 centistokes, an immersion solution of HPMC from which a capsule shell is to be obtained by a dipping technique has a too low viscosity to shape the capsule shell. With a viscosity of more than 5.4 centistokes, an immersion solution has a too high viscosity, which requires to reduce the amount of HPMC blended which in turn, requires to increase the proportion of the gelling agent blended, failing to achieve the object of the invention.

Such low viscosity EPMC is commercially available as TC-5M type HPMC (2% aqueous solution viscosity 4.5 centistokes at 20° C.) and TC-5E type HPMC (2% aqueous solution viscosity 3.0 centistokes at 20° C.) from Shin-Etsu Chemical Co., Ltd. These HPMC products may be used alone or suitably blended to form a mixture having a viscosity of 3.0 to 4.6 centistokes. Alternatively, such a EPMC product may be blended with another HPMC product having higher or lower viscosity (by itself outside the scope of the invention) to form a mixture having an optimum viscosity as defined above.

Carrageenan is blended as the gelling agent. Carrageenan generally includes three types, iota ($\iota$), kappa ($\kappa$) and lambda ($\lambda$). Among these, $\iota$-carrageenan and $\kappa$-carrageenan having a gelling ability may be used, with the carrageenan being preferred.

The co-gelling agent for assisting in gelation of carrageenan is a potassium ion, a calcium ion or both. As a general rule, a calcium ion is used for $\iota$-carrageenan and a potassium ion is used for $\kappa$-carrageenan. It is most preferred to use $\kappa$-carrageenan as the gelling agent and a potassium ion as the co-gelling agent. The potassium ion may be blended in the form of a water-soluble compound such as potassium chloride, potassium phosphate and potassium citrate. The calcium ion may also be blended in the form of a water-soluble compound such as calcium chloride.

In the capsule shell of the invention containing the above-defined HRMC base, carrageenan gelling agent and co-gelling agent in the above-defined proportion, there may be further blended various additives such as coloring agents (e.g., dyes and pigments), opaque agents, and flavors in conventional amounts.

The capsule shell of the present invention is prepared by drying an aqueous solution comprising the above-defined HPMC base, carrageenan gelling agent, co-gelling agent and optional additives.

The amount of HPMC blended in the aqueous solution is 18 to 28% by weight, preferably 19 to 25% by weight. Several inconvenient problems occur if the amount of HPMC blended is outside this range. The capsule shell of the invention is prepared by dissolving the HPMC, gelling agent, co-gelling agent and optional additives in water to form an aqueous immersion solution, immersing molding pins in the immersion solution, withdrawing the pins from the solution with the solution adhering to the periphery of the pins, and drying the adhering solution. If the amount of HPMC blended is less than 18% by weight, the proportion of the gelling agent blended becomes relatively high, failing to achieve the object of the invention. If the amount of HPMC blended is more than 28% by weight, the proportion of the gelling agent blended becomes relatively low, but the immersion solution has a too high viscosity to shape capsule shells by the dipping technique.

The amount of carrageenan blended in the aqueous solution is 0.01 to 0.09% by weight, preferably 0.05 to 0.07% by weight. If the amount of carrageenan blended is less than 0.01% by weight, no satisfactory degree of gelation is achieved and shells of sufficient gage cannot be formed by the dipping technique. If the amount of carrageenan blended exceeds 0.09% by weight, the capsule shell loses disintegration ability in the presence of calcium ions, failing to achieve the object of the invention.

The amount of co-gelling agent blended in the aqueous solution is 0.05 to 0.6% by weight, preferably 0.06 to 0.1% by weight in ionic amount. If the amount of co-gelling blended is less than 0.05% by weight, no satisfactory gelation of carrageenan is achieved and shells of sufficient gage cannot be formed by the dipping technique. If the amount of co-gelling agent blended exceeds 0.6% by weight, a gelled film forms in an aqueous immersion solution, shell formation by the dipping technique is difficult, and shells, even formed, are low in disintegration ability.

Preferably, the aqueous solution comprising the above-defined HPMC base, carrageenan gelling agent and co-gelling agent in the above-defined proportion has a viscosity of 500 to 3000 centistokes at 54° C., more preferably 800 to 2000 centistokes at 54° C.

The capsule shell of the present invention is prepared by a well-known dipping technique as used in the manufacture of conventional gelatin capsule shells. More particularly, medical hard capsules are prepared by blending the HPMC, gelling agent, co-gelling agent and optional additives in water to form the above-defined aqueous solution or immersion solution, once immersing molding pins in the immersion solution, withdrawing the pins from the solution with the solution adhering to the periphery of the pins, drying the adhering solution to form capsule shells (body or cap), and removing the shells from the pins. The shells are cut to a suitable size if necessary. A pair of body and cap shells are mated to form a capsule. In this way, the capsule shell of the invention is available in the form of a hard capsule.

In shaping the capsule shell by the above-mentioned dipping technique, the immersion solution in which shaping pins are immersed is preferably set at a temperature of 48° to 55° C., especially 51° to 53° C. Outside this temperature range, the immersion solution would have a finely varying jelly viscosity and thickly or thinly adhere to the pins, failing to form shells of uniform gage. Thereafter the immersion solution adhering to the pins is preferably dried at a temperature of 25° to 35° C. for 40 to 60 minutes. Through the drying step, the immersion solution adhering to the pins is concentrated to form hard shells around the pins. Other conditions may be the same as used in the manufacture of conventional gelatin shells.

The thus obtained capsule shell of the invention contains 79.6 to 98.7% by weight, preferably 79.8 to 98.7% by weight of the HPMC as a base, 0.03 to 0.5% by weight, preferably 0.14 to 0.38% by weight of carrageenan as a gelling agent and 0.14 to 3.19% by weight, preferably 0.17 to 0.5% by weight of a potassium ion and/or a calcium ion as a co-gelling agent. It is noted that the capsule shell of the invention generally has a water content of about 1 to 8% by weight, preferably 1 to 6% by weight, ensuring formation of hard capsules with a low water content.

Though the invention is not bound to the theory, the reason why the capsule shell of the invention maintains satisfactory disintegration ability even in the presence of calcium ions is as follows.

Figure 1B:
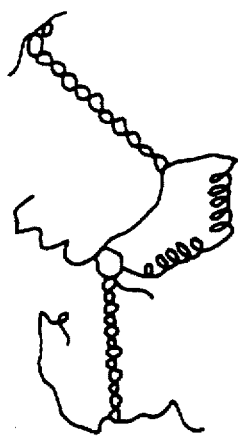
Figure 1C:
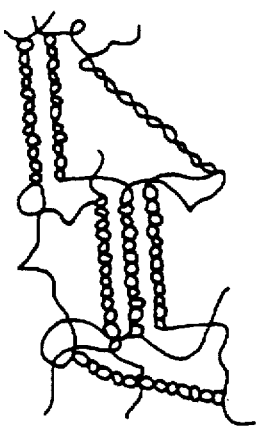

As mentioned above, the shapability of HPMC is improved by gelling carrageenan as the gelling agent with the co-gelling agent. The gelation of carrageenan follows the mechanism schematically shown in FIG. 1 that carrageenan molecules form double helix structures with the aid of the co-gelling agent (FIG. 1B) to form a three-dimensional network. If the thus gelled carrageenan comes in contact with a calcium ion, the double helix structures increase to strengthen the three-dimensional network (FIG. 1C). Also crosslinking occurs between adjacent sulfate groups in adjacent double helix structures to stabilize the three-dimensional network. Then the gel increases its hardness to detract from solubility or disintegration ability. However, in the capsule shell of the present invention, by using a HPMC having a relatively low viscosity as a base, increasing the proportion of HPMC used, increasing the amount of the co-gelling agent blended, and minimizing the proportion of carrageenan gelling agent within a sufficient range to insure good shapability, the amount of carrageenan relative to HPMC is set at a very low level. Then even when double helix structures of carrageenan increase upon contact with calcium ions and crosslinking occurs between sulfate groups in double helix structures, the interstice structure resulting from tangling of carrageenan molecules is maintained in a relatively coarse state so that strong gelation does not occur. In this way, satisfactory disintegration ability is maintained.

The capsule shell of the invention containing the above-defined HPMC baser carrageenan gelling agent and co-gelling agent in the above-defined proportion exhibits satisfactory disintegration ability even in an environment where calcium ions are present. In one preferred embodiment, the capsule shell of 0.1 mm thick should preferably have an opening time within 4 minutes, more preferably within 2–½ minutes when immersed in an aqueous solution of 0.1M potassium chloride at 37° C. The potassium ion inhibits dissolution of carrageenan through a similar mechanism to the inhibitory mechanism of the calcium ion and rather to a greater extent than the calcium ion. Then the dissolution of a shell in the presence of potassium ions can represent the dissolution of a shell in the presence of calcium ions. Then a shell having satisfactory dissolution characteristics in an aqueous solution of potassium chloride will exhibit satisfactory disintegration ability comparable to that of conventional gelatin shells even in an environment where much calcium ions are present. It is thus understood that the shell of the invention having a dissolution time as defined above of more than 4 minutes will still have practically acceptable dissolution property in the presence of calcium ions.

The capsule shell of the invention has improved shapability and disintegration ability comparable to conventional gelatin shells even in special conditions where much calcium ions are present. HPMC capsules of the inventive shell will effectively disintegrate in the stomach even when they are administered after drinking milk containing much calcium ions, achieving equivalent performance to conventional gelatin capsules. Then the invention enables to take full advantage of HPMC-base hard capsules.

EXAMPLE

Examples of the invention are given below by way of illustration and not by way of limitation. All percents are by weight.

Example 1 and Comparative Example 1

Potassium chloride was dissolved in pure water at about 75° C. With stirring, κ-carrageenan and a coloring agent (titanium oxide) were added to the solution and dissolved therein. With stirring, hydroxypropylmethyl cellulose (HPMC) was added to the solution and dispersed therein. The solution was cooled to a temperature of 50° C. and further agitated for dissolving the HPMC therein. The solution was then allowed to stand for deaeration. In this way, two immersion solutions were obtained as shown in Table 1.

A conventional capsule shell forming apparatus was charged with the immersion solution which was maintained at 52° C. The apparatus was operated in accordance with a conventional dipping technique to prepare No. 2 capsule shells of the shell composition shown in Table 1 having a thickness of 0.1 mm. In this way, two types of capsule shells were obtained.

TABLE 1

|  |  |  | Example 1 | Comparative Example 1 |
|---|---|---|---|---|
| Immersion solution | HPMC | TC-5R | — | 16% |
|  |  | TC-5MW | 10% | — |
|  |  | TC-5EW | 10% | — |
|  |  | Viscosity | 3.8 cst | 6.0 cst |
|  | κ-carrageenan |  | 0.08% | 0.2% |
|  | Potassium chloride |  | 0.11% | 0.1% |
|  | (potassium ion) |  | (0.06%) | (0.05%) |
|  | Titanium oxide |  | 0.77% | 0.62% |
| Capsule shell | HPMC |  | 90.63% | 89.83% |
|  | κ-carrageenan |  | 0.36% | 1.12% |
|  | Potassium chloride |  | 0.50% | 0.56% |
|  | (potassium ion) |  | (0.26%) | (0.29%) |
|  | Titanium oxide |  | 3.51% | 3.49% |
|  | Water |  | 5% | 5% |

Note: TC-5R, TC-5MW and TC-5EW are trade names of HPMC manufactured by shin-Etsu Chemical Co., Ltd. TC-5R has a viscosity of 6.0 centistokes; TC-5MW has a viscosity of 4.5 centistokes; and TC-5EW has a viscosity of 3.0 centistokes, as measured in 2% aqueous solution at 20° C. The viscosity of Example I is that of a 1/1 mixture of TC-5MW and TC-5EW.

The capsules were filled with 0.3 g of corn starch and immersed in an aqueous solution of 0.1M potassium chloride at 37° C. The opening time was measured by means of a disintegration tester as prescribed in the Pharmacopoeia of Japan. Three measurements were taken and an average was calculated. The results are shown in Table 2. As a reference, a conventional gelatin capsule was similarly measured for opening time, with the results shown in Table 2.

TABLE 2

| Capsule | Opening time (min.) | | | |
|---|---|---|---|---|
| Gelatin | 1.3 | 1.5 | 1.5 | av. 1.4 |
| Comparative Example 1 | 4.2 | 4.5 | 6.8 | av. 5.2 |
| Example 1 | 1.9 | 2.2 | 2.4 | av. 2.2 |

Separately, the capsules were filled with 0.7 g of copper wire as a weight and immersed in milk at 37° C. The opening time was measured by means of a disintegration tester as prescribed in the Pharmacopoeia of Japan. Three measurements were taken and an average was calculated. The results are shown in Table 3. As a reference, a conventional gelatin capsule was similarly measured for opening time, with the results shown in Table 3.

TABLE 3

| Capsule | Opening time (min.) | | | |
|---|---|---|---|---|
| Gelatin | 2 | 3 | 3 | av. 2.7 |
| Comparative Example 1 | 15 | 16 | 18 | av. 16.3 |
| Example 1 | 3 | 3 | 4 | av. 3.3 |

It is seen from Table 3 that the capsule shell of the invention exhibits disintegration ability equivalent to the conventional gelatin capsule even in milk containing much calcium ions.

Next, the capsule of Example 1 and a conventional gelatin capsule were evaluated for disintegration ability in the first and second fluids prescribed in the Pharmacopoeia of Japan, Section 12. The capsules each were filled with 300 mg of a mixture of 20 parts by weight of acetaminophen and 280 parts by weight of corn starch. The capsules were immersed in the first and second fluids. While stirring the test solution by rotating a paddle at 100 rpm, the percent leaching of the contents was measured. The results are plotted in the graphs of FIGS. 2 and 3.

Figure 2:
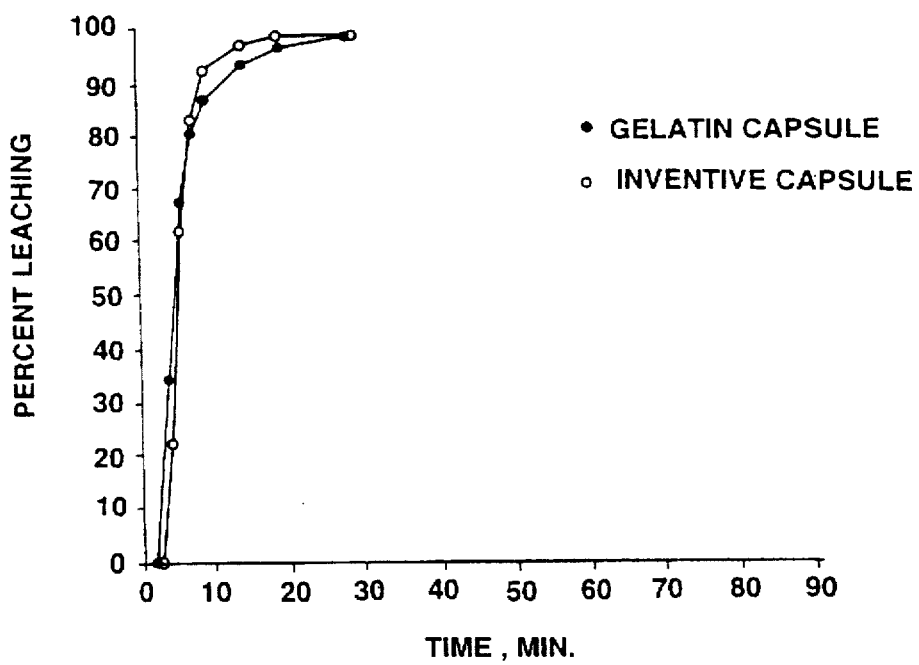
FIG. 2 is a graph showing the percent leaching of the contents from a capsule of Example 1 and a conventional gelatin capsule when they were immersed in the first solution prescribed in the Pharmacopoeia of Japan.
Figure 3:
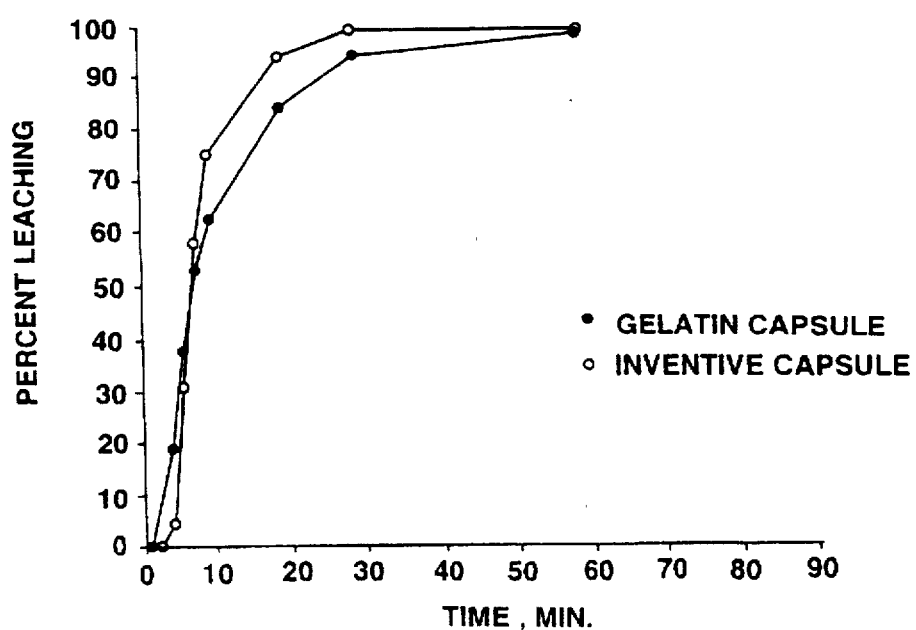
FIG. 3 is a graph showing the percent leaching of the contents from a capsule of Example 1 and a conventional gelatin capsule when they were immersed in the second solution prescribed in the Pharmacopoeia of Japan.

It is seen from FIGS. 2 and 3 that the capsule of Example 1 has an equivalent disintegration ability to that of the conventional gelatin capsule in both the first and second fluids prescribed in the Pharmacopoeia of Japan. This suggests that the hard capsules of the shell according to the invention are useful as medical capsules. Examples 2-5 and Comparative Example 2-6

Potassium chloride was dissolved in pure water at about 75° C. With stirring, κ-carrageenan was added to the solution and dissolved therein. With stirring, hydroxypropylmethyl cellulose (HPMC) was added to the solution and dispersed therein. The solution was cooled to a temperature of 50° C. and further agitated for dissolving the HPMC therein. The solution was then allowed to stand for deaeration. In this way, nine immersion solutions were obtained as shown in Table 4.

The immersion solution was maintained at 52° C. Nine types of capsule films of the shell composition shown in Table 4 having a thickness of 0.1 mm were prepared by conventional dipping technique from the immersion solutions.

The capsule shell films (10 mm×20 mm) were immersed in milk at 37° C. The dissolving time was measured by means of a disintegration tester as prescribed in the Pharmacopoeia of Japan. Three measurements were taken and an average was calculated. The results are shown in Table 5. As a reference, a conventional gelatin capsule film was similarly measured for dissolving time, with the results shown in Table 5.

TABLE 4

|  |  |  | Example | | | | Comparative Example | | | | |
|---|---|---|---|---|---|---|---|---|---|---|---|
|  |  |  | No. 2 | No. 3 | No. 4 | No. 5 | No. 2 | No. 3 | No. 4 | No. 5 | No. 6 |
| Immersion solution | HPMC | TC-5R |  |  |  |  |  |  | 16% |  | 10% |
|  |  | TC-5MW |  |  | 10% | 18% |  | 16% |  |  |  |
|  |  | TC-5EW | 28% | 25% | 10% |  | 16% |  |  | 25% |  |
|  |  | Viscosity | 3.0 cst | 3.0 cst | 3.8 cst | 4.5 cst | 3.0 cst | 4.5 cst | 6.0 cst | 3.0 cst | 6.0 cst |
|  | κ-carrageenan |  | 0.01% | 0.06% | 0.08% | 0.08% | 0.20% | 0.20% | 0.20% | 0.15% | 0.20% |
|  | Potassium chloride |  | 1.0% | 0.11% | 1.11% | 0.11% | 0.10% | 0.10% | 0.10% | 0.10% | 0.10% |
|  | (potassium ion) |  | (0.5%) | (0.06%) | (0.06%) | (0.06%) | (0.05%) | (0.05%) | (0.05%) | (0.05%) | (0.05%) |
| Capsule shell | HPMC |  | 95.55% | 98.33% | 98.07% | 97.97% | 97.18% | 97.18% | 97.18% | 98.01% | 96.12% |
|  | K-carrageenan |  | 0.03% | 0.24% | 0.40% | 0.44% | 1.22% | 1.22% | 1.22% | 0.59% | 1.92% |
|  | Potassium chloride |  | 3.42% | 0.43% | 0.53% | 0.59% | 0.60% | 0.60% | 0.60% | 0.40% | 0.96% |
|  | (potassium ion) |  | (1.79%) | (0.33%) | (0.28%) | (0.31%) | (0.32%) | (0.32%) | (0.32%) | (0.21%) | (0.50%) |

TABLE 4-continued

|  | Example | | | | Comparative Example | | | | |
| --- | --- | --- | --- | --- | --- | --- | --- | --- | --- |
|  | No. 2 | No. 3 | No. 4 | No. 5 | No. 2 | No. 3 | No. 4 | No. 5 | No. 6 |
| Water | 1% | 1% | 1% | 1% | 1% | 1% | 1% | 1% | 1% |

Note: TC-5R, TC-5MW and TC-5EW are trade names of HPMC manufactured by Shin-Etsu Chemical Co., Ltd. TC-5R has a viscosity of 6.0 centistokes; TC-5MW has a viscosity of 4.5 centistokes; and TC-5EW has a viscosity of 3.0 centistokes, as measured in 2% aqueous solution at 20° C. The viscosity of Example 4 is that of a 1/1 mixture of TC-5MW and TC-5EW.

TABLE 5

| Film | | Dissolving time (min.) | | | |
| --- | --- | --- | --- | --- | --- |
| Example | No.2 | 4 | 5 | 5 | av. 4.7 |
|  | No.3 | 6 | 6 | 7 | av. 6.3 |
|  | No.4 | 7 | 8 | 9 | av. 8.0 |
|  | No.5 | 9 | 9 | 9 | av. 9.0 |
| Comparative Example | No.2 | 28 | 28 | 28 | av. 28.3 |
|  | No.3 | 25 | 28 | 28 | av. 27.0 |
|  | No.4 | 21 | 23 | 27 | av. 23.7 |
|  | No.5 | 14 | 15 | 15 | av. 14.7 |
|  | No.6 | >60 | >60 | >60 | — |
| Gelatin |  | 3 | 4 | 5 | av. 4.0 |

It is seen from Table 5 that the capsule shell film of the invention exhibits disintegration ability even in milk containing much calcium ions.

Comparative Example 7

Potassium chloride was dissolved in pure water at about 75° C. With stirring, κ-carrageenan and a coloring agent (titanium oxide) were added to the solution and dissolved therein. With stirring, hydroxypropylmethyl cellulose (HPMC) having a viscosity of 5.87 centistokes as measured in a 2% aqueous solution at 20° C. was added to the solution and dispersed therein. The solution was cooled to a temperature of 50° C. and further agitated for dissolving the HPMC therein. The solution was then allowed to stand for deaeration. In this way, an immersion solution containing 20% by weight of the EPMC, 0.08% by weight of κ-carrageenan and 0.06% by weight of potassium ion was obtained.

A viscosity of the immersion solution was too high for the capsule shell having a thickness of 0.1 mm to be formed by the dipping technique.

We claim:

1. A capsule shell comprising 79.6 to 98.7% by weight of a hydroxypropylmethyl cellulose, 0.03 to 0.5% by weight of carrageenan, and 0.14 to 3.19% by weight of a potassium ion and/or a calcium ion, said capsule shell being prepared by drying an aqueous solution comprising 18 to 28% by weight of hydroxypropyl-methyl cellulose having a viscosity of 2.4 to 5.4 centistokes as measured in a 2% aqueous solution at 20° C. as a base, 0.01 to 0.09% by weight of carrageenan as a gelling agent, and 0.05 to 0.6% by weight of at least one ion selected from the group consisting of potassium and calcium ions as a co-gelling agent.

2. The capsule shell of claim 1 Which comprises 1 to 8% by weight of water.

3. The capsule shell of claim 1 wherein said carrageenan gelling agent is κ-carrageenan and the co-gelling agent is a potassium ion.

4. The capsule shell of claim 1 wherein the viscosity of the hydroxypropylmethyl cellulose is 3.0 to 4.6 centistokes as measured in a 2% aqueous solution at 20° C.

5. The capsule shell of claim 1 wherein the viscosity of the aqueous solution is 500 to 3000 centistokes at 54° C.

6. A capsule shell comprising 79.8 to 98.7% by weight of a hydroxypropylmethyl cellulose, 0.14 to 0.38% by weight of carrageenan, and 0.17 to 0.5% by weight of a potassium ion and/or a calcium ion, said capsule shell being prepared by drying an aqueous solution comprising 19 to 25% by weight of hydroxypropyl-methyl cellulose having a viscosity of 2–4 to 5.4 centistokes as measured in a 2% aqueous solution at 20° C. as a base, 0.05 to 0.07% by weight of carrageenan as a gelling agent, and 0.06 to 0.1% by weight of at least one ion selected from the group consisting of potassium and calcium ions as a co-gelling agent.

7. The capsule shell of claim 1 which has a thickness of 0.1 mm and has an opening time within 4 minutes when immersed in an aqueous solution of 0.1M potassium chloride at 37° C.

8. The capsule shell of claim 7 wherein the opening time is within 2–2/1 minutes when immersed in an aqueous solution of 0.1M potassium chloride at 37° C.

* * * * *